United States Patent

Pace et al.

[11] Patent Number: 5,522,978
[45] Date of Patent: Jun. 4, 1996

[54] MONENSIN AMIDES FOR SODIUM-SELECTIVE ELECTRODES

[75] Inventors: Salvatore J. Pace; Chengrong Wang, both of Wilmington, Del.

[73] Assignee: E. I. Du Pont de Nemours and Company, Wilmington, Del.

[21] Appl. No.: 318,959

[22] Filed: Oct. 6, 1994

Related U.S. Application Data

[63] Continuation of Ser. No. 154,659, Nov. 18, 1993, abandoned.

[51] Int. Cl.$^6$ .................................................. G01N 27/26
[52] U.S. Cl. ..................... 204/418; 204/403; 204/416; 204/430; 252/62.2; 252/500; 549/334
[58] Field of Search .................... 204/418, 416, 204/403, 420, 282, 283; 252/62.2, 500; 549/334

[56] References Cited

U.S. PATENT DOCUMENTS

| 4,933,048 | 6/1990 | Lauks | 204/1.11 |
| 5,284,568 | 2/1994 | Pace et al. | 204/403 |

OTHER PUBLICATIONS

Maruyama et al., Enantiomer Recognition of Organic Ammonium Salts by Podadn and Crown Type Monesin Amides: New Synthetic Strategy for Chiral Receptors, pp. 805–805, Tetrahedron vol. 48, No. 5, 1992.

Brandchaud, B. P., and Choi, Y. C., Synthesis of Monensin. Reconstruction from Degradation Products, *J. Org. Chem.* 53, 4641–4643, 1988.

Kimura, K. et al., Unsymmetrical Calix[4]Arene Ionophore/Silicone Rubber Composite Membranes for High-Performance Sodium Ion–Sensitive Field–Effect Transistors, *Anal. Chem.*, 64, 2508–2511, 1992.

Lehn, Jean–Marie, Supramolecular Chemistry: Receptors, Catalysts, and Carriers, *Science*, 227, No.4689, 849–856, Feb. 22, 1986.

Maruyama, K., et al., New Chiral Host Molecules Derived from Naturally Occurring Monensin Ionophore, *J. Chem. Soc.*, Chem. Commun., 864–865, 1989.

Maruyama, K., et al., Enantiomer Recognition of Organic Ammonium Salts by Podand–And Crown–Type Monensin Amides: New Synthetic Strategy for Chiral Receptors, *Tetrahedron*, 48, No. 5, 805–818, 1992.

Suzuki, K., et al., Ion–Selective Electrodes Based on Natural Carboxylic Polyether Antibiotics, *Anal. Chem.*, 60, 1714–1721, 1988.

Tamura, H., et al., Coated Wire Sodium–and Potassium–Selective Electrodes Based on Bis(crown ether) Compounds, *Anal. Chem.*, 54, 1224–1227, 1982.

Tohda, K., et al., A Sodium Ion Selective Electrode Based on a Highly Lipophilic Monensin Derivative and Its Application to the Measurement of Sodium Ion Concentrations in Serum, *Analytical Sciences*, 6, 227–232, Apr. 1990.

*Primary Examiner*—Bruce F. Bell

[57] ABSTRACT

This invention relates to sodium-selective agents which are monensin amide derivatives and sodium-selective electrodes having sodium-selective membranes containing such monensin amide derivatives. This invention further relates to multisensor flow assemblies incorporating such a monensin amide derivative in a sodium-selective electrode.

13 Claims, 6 Drawing Sheets

FIG. 1

MONENSIN AMIDES FOR SODIUM-SELECTIVE ELECTRODES

This is a continuation of application Ser. No. 08/154,659, filed Nov. 18, 1993, now abandoned.

FIELD OF THE INVENTION

This invention is related to ion selective agents useful in preparing membranes for ion selective electrodes, and more particularly, monensin amide derivatives which are useful as sodium-selective agents in sodium-selective membranes for sodium ion selective electrodes.

BACKGROUND OF THE INVENTION

Electrochemical measurements are widely used to determine the concentration of specific substances in fluids. These devices, referred to as ion-selective electrodes (ISEs), can be employed in a wide variety of potentiometric ion determinations, including, for example, the activity of fluoride ion in drinking water, the pH of process streams, and the determination of electrolytes in blood serum.

In the health care field, and, in particular, in the area of clinical diagnostics, ISEs are commonly used to measure the activity or concentration of various ions and metabolites present in blood, plasma or serum, urine, and other biological fluids. For example, ISEs are typically used to determine $Na^+$, $Ca^{++}$, $Mg^{++}$, $K^+$, $Cl^-$, $Li^+$ ions as well as the pH, and carbon dioxide content in such fluids.

Conventional ion-selective electrodes are typically composed of an ion-selective membrane, an internal filling solution or electrolyte, and an internal reference electrode. Ion-selective electrodes can be classified according to the nature of the membrane material, and include solid state membrane electrodes, glass membrane electrodes, liquid membrane electrodes having charged ion-selective agents, and neutral liquid membrane electrodes having membranes formed from an organic solution containing an electrically neutral, ion-selective agent such as an ionophore held in an inert polymer matrix. An external reference electrode used in conjunction with the ISE to effect the assay measurement is typically a metal/metal halide electrode such as Ag/AgCl.

When the ion selective membrane electrode is exposed or subjected to a sample solution, the ion of interest is selectively transferred from the sample solution into the membrane. The charge associated with the ions generate a potential that can be mathematically related to the concentration or activity of the ion content in the sample. If the membrane is ion specific or ideally selective toward the ion of interest, the potential difference is a linear function of the logarithm of the activity ratio of the ion activity (Nernst equation). A semi-empirical extension of the Nernst Equation (Nikolskii Eisenmann equation) for EMF may be utilized for non-ideal conditions. By "EMF" is meant the electrical potential difference between the internal ion sensing electrode and external reference electrode, the electrodes being electrolytically connected by means of the sample solution at zero or near zero current flow.

Conventional ISEs are typically bulky, expensive, difficult to clean and maintain, and tend to require an undesirably large volume of biological fluid. For these reasons, much attention has been directed towards developing more reliable ISEs of smaller size. These relatively small ISEs, referred to as ion-selective sensors or biosensors, can be inexpensively mass produced using techniques similar to those employed in the manufacture of electronic components, including, for example, photolithography, screen printing, and ion-implantation.

Ion-selective sensors and biosensors can be manufactured at much lower production cost than conventional ISEs, making it economically feasible to offer a single-use or limited-use disposable device, thereby eliminating the difficulty of cleaning and maintaining conventional ISEs. The reduced size of ion-selective sensors further serve to reduce the required volume of patient sample. Generally, a sensor can be either a miniature version of a conventional electrode or a device constructed using one or more of the above mentioned techniques. Maximum accuracy of the analytical or diagnostic result is obtained when the sensor responds only to the concentration or activity of the component of interest and has a response independent of the presence of interfering ions and/or underlying membrane matrix effects. The desired selectivity is often achieved by an ion-selective membrane containing an ion-selective agent such as an ionophore positioned over an electrical conductor.

Generally, ion-selective membranes are formed from a plasticized polymer matrix, such as polyvinyl chloride, which contains the ionophore selective for the ion of interest. For example, natural polyether antibiotic monensin is a known ionophore which is selective for sodium ($Na^+$) ions (Lutz, W. K., et al., Helv Chim ACTA, 53, 1741 (1970).

Monensin ester derivatives such as methyl, ethyl, and butyl monensin esters have also been used as ionophores or sodium-selective agents in membranes for ISE applications. For example, highly lipophilic monensin derivatives have been reported in ISE applications for serum $Na^+$ determinations (Tohda, K. et al. Analytical Sciences, vol. 6 (April 1990).

One known limitation of monensin ester derivatives is their low selectivity for $Na^+$ relative to potassium ions ($K^+$). This is not particularly troublesome in human serum samples where a selectivity factor of $K_{Na/K}=0.5$ for sodium relative to potassium ion results in an insignificant potassium error due to the presence in human serum of a maximum potassium concentration range of 2 to 8 mEq/L and a nominal sodium concentration range of 145 mEq/L. In contrast, urine samples can contain potassium concentrations ranging as low as 1 mEq/L or less up to 100 mEq/L along with relatively low sodium levels of 10 mEq/L. Thus, accurate determinations of sodium ions in urine samples can be troublesome when made using known monensin ester derivatives having low selectivity for $Na^+$ relative to potassium ions ($K^+$). This problem is typically handled by performing parallel potassium ion determinations and correcting any inaccurate sodium determinations.

Other known synthetic ionophores or ion-selective agents for sodium include polyether diamide, biscrown ether (Tamura et al., Anal. Chem., 64, 2508 (1992)), cryptand (Lehn et al., Science, vol. 227, no. 4689, p.849 (1985)), and calixarene (Kimura et al., Anal. Chem., 64, p. 2508 (1992)). However, the effectiveness of these sodium ionophores can be affected by interfering substances including drugs and interfering cations present in biological samples, such as urine.

Maryuma, K. et al., Enantiomer Recognition of Organic Ammonium Salts by Podand and Crown Type Monensin Amides: New Synthetic Strategy for Chiral Receptors, Tetrahedron, vol. 48., no. 5, pp. 805–818 (1992) disclose monensin amide derivatives exhibiting the same $Na^+$ selectivity as biological monensin and its ester. Maryuma, K. et al. do not mention the monensin derivatives of the present invention. Maryuma, K. et al., New Chiral Host Molecules

Derived From Naturally Occurring Monensin Ionophore, J. Chem. Soc., Commun., p. 864 (1989) disclose monensin derivatives having neutral terminal groups which show enantiomeric selectivity for several amine salts, whereas natural monensin could not discriminate between the enantiomers. Neither of the Maryuma, K. et al. references mention or suggest the monensin amide derivatives of the present invention such as the hexadecyl monensin amide or methyl hexyl monensin amide sodium-selective agents.

There is a need for a sodium-selective agent for use in an ISE which provides for adequate sodium selectivity and which minimizes or reduces the effects of interfering substances such as drugs and interfering cations present in biological samples such as urine samples.

SUMMARY OF THE INVENTION

The present invention provides for sodium-selective agents and sodium-selective electrodes which overcome many of the disadvantages of known sodium-selective agents and electrodes.

In one aspect, the present invention is related to a sodium-selective agent useful for determining sodium in biological samples having the structure:

wherein $R_1$ is H or an alkyl group having less than or equal to six carbon atoms, wherein the alkyl group is straight chained or branched and can contain heteroatoms; and $R_2$ is an alkyl group having greater than or equal to six carbon atoms wherein the alkyl group is straight chained or branched and can contain heteroatoms.

In a second aspect, the present invention is related to a sodium-selective agent useful for determining sodium in biological samples having the structure:

In a third aspect, the present invention is related to a sodium-selective agent useful for determining sodium in biological samples having the structure:

In a further aspect, the present invention is related to a sodium-selective electrode for determining an ion in a biological sample which comprises an electrical conductor and an ion-selective membrane separating the conductor from the sample wherein the membrane comprises:

(a) a polymer material; and (b) a sodium-selective agent incorporated into the polymer material, the sodium-selective agent having the structure:

wherein $R_1$ is H or an alkyl group having less than or equal to six carbon atoms, wherein the alkyl group is straight chained or branched and can contain heteroatoms; and $R_2$ is an alkyl group having greater than or equal to six carbon atoms wherein the alkyl group is straight chained or branched and can contain heteroatoms.

A further aspect of the present invention is related to a sodium-selective electrode for determining sodium in a biological sample which comprises an electrical conductor and an ion selective membrane separating the conductor from the sample wherein the membrane comprises:

(a) about 25% by weight carboxylated polyvinyl chloride;

(b) about 2% by weight hexadecyl monensin amide or methyl hexyl amide monensin; and (c) about 50% by weight dioctyl adipate.

The present invention is further related to a multisensor cell assembly for determining an ion of interest in a biological sample comprising:

a substrate having a surface with a reference electrode and at least one ion-selective electrode formed thereon, the ion-selective electrode having an electrical conductor and an ion selective membrane separating the conductor from the sample, wherein one ion-selective electrode has a membrane comprising a polymer material and a sodium-selective agent incorporated into the polymer material, the sodium-selective agent having the structure:

wherein $R_1$ is H or an alkyl group having less than or equal to six carbon atoms, wherein the alkyl group is straight chained or branched and can contain heteroatoms; and $R_2$ is an alkyl group having greater than or equal to six carbon atoms wherein the alkyl group is straight chained or branched and can contain heteroatoms; and an elastomeric component positioned on the surface of the substrate defining a reference and sensor flow channels, the reference flow channel having means for passing reference liquids over the reference electrode, the sensor flow channel having means for passing sample liquids over each ion-selective electrode, the reference and sensor flow channels defining a common outlet for removing liquids from the cell.

The monensin amide derivatives of the present invention provide for adequate sodium selectivity relative to potassium to accurately determine sodium ions in biological samples and, further, surprisingly and unexpectedly reduce or minimize the effects of interfering substances such as drugs and/or interfering cations present in such biological samples, particuarly urine.

BRIEF DESCRIPTION OF THE DRAWINGS

The invention will be better understood if reference is made to the accompanying drawings, in which.

DESCRIPTION OF THE INVENTION

The sodium-selective electrode (ISE) of the present invention has a sodium-selective membrane which contains a sodium-selective agent which offers significant advantages over known sodium-selective agents in that the ISE of the present invention provides for adequate sodium selectivity relative to potassium and further reduces or minimizes the effect of interfering substances such as drugs or interfering cations present in biological samples, particularly urine samples. The sodium-selective membrane is composed of a polymer and a sodium-selective agent which is incorporated into the polymer. The sodium-selective electrode further comprises an electrically conductive material (electrical conductor).

By "ion-selective electrode" (ISE) is meant a potentiometric electrochemical sensor, the potential of which is related to the activity or concentration of an ion of interest in a sample. Generally, the potential is linearly dependent on the logarithm of the activity of the ion of interest. The activity of an ion of interest is defined as its concentration multiplied by an activity coefficient, where the activity coefficient is generally known or available in the art.

By "sodium-selective electrode" is meant an ISE where the ion of interest is a sodium.

By "biological sample" is meant any fluid of biological origin including fluids which have been chemically and/or physically treated, diluted, or concentrated prior to analysis. Examples of biological samples include serum, urine, plasma, whole blood, cerebrospinal fluid, amniotic fluid, saliva, and tears.

By "ion of interest" is meant an ion to be determined in a biological sample using an ion-selective electrode.

A general discussion of the principles of potentiometric ion sensors is provided by Oesch et al., "Ion-Selective Membranes for Clinical Use," Clinical Chemistry, Vol. 32, No. 8, pp. 1448–1459, (1986).

Typically sodium-selective electrodes have a membrane comprising a polymer material and a sodium-selective agent. Additional optional components of the membrane include a plasticizer such as dioctyl adipate, for rendering the membrane pliable as well as other components.

By "polymer material" is meant any polymer suitable for use in preparing sodium ISE's. A variety of polymers can be utilized including, but not limited to, polymethyl acrylate and other acrylates, silicone rubbers, polycarbonate cellulose, cellulose ester, poly(vinyl acetate), polyurethane, poly(vinyl butyral), polyvinyl chloride, carboxylated polyvinyl chloride, and other copolymers of vinyl chloride. By cellulose ester is meant all ester derivatives of cellulose including, but not limited to, cellulose acetate, cellulose butyrate, and other members of a homologous series. By poly(vinyl butyral) is meant a copolymer of vinyl butyral, vinyl alcohol, and vinyl acetate. Carboxylated polyvinyl chloride is preferred.

The amount of polymer material used is that amount sufficient to produce a membrane of suitable thickness and structural integrity for use as an ion-selective electrode. The preferred amount of polymer material utilized in the sodium-selective electrode of the present invention is about 20% by weight. The thickness of the sodium-selective membrane of the present invention can vary from about 1μ to about 1000μ in thickness and is preferably about 50μ in thickness.

By "sodium-selective agent" is meant any substance which provides for selective interaction with sodium. Examples of such sodium-selective agents include ionophores and other sodium-selective agents. Examples of known sodium-selective agents include, naturally, occurring monensin, monensin ester derivatives such as methyl, ethyl, butyl, and dodecyl ester monensins, polyether diamide, biscrown ether, cryptand, and calixarene.

The sodium-selective agent of the present invention is a compound having a structure comprising a monensin amide derivative as follows:

$R_1$ can be H or an alkyl group having less than or equal to six carbon atoms, wherein the alkyl group can be straight chained or branched and can contain heteroatoms such as O, N, and S.

$R_2$ can be an alkyl group having greater than or equal to six carbon atoms, wherein the alkyl group can be straight chained or branched and can contain heteroatoms such as O, N, and S. Preferably $R_1$ is H and $R_2$ is $C_{16}H_{33}$ (hexadecyl amide monensin) or $C_6H_{13}$ (methyl hexyl amide monensin). Hexadecyl amide monensin is particularly preferred.

The amount of sodium-selective agent incorporated into the sodium-selective electrode of the present invention can vary from 1% to 10% by weight. An amount of from about 2% by weight to about 5% by weight is preferred. The amount of sodium-selective agent employed can impact the use life of the membrane, where use life is defined as the number of samples assayed without compromising analytical quality.

The sodium-selective membrane of the electrode of the present invention can be prepared by mixing a suitable amount of polymer material dissolved in an appropriate solvent with a suitable amount of sodium-selective agent to produce an ion-selective polymer material. The solvent used can be any solvent commonly used to prepare conventional membranes and can include, for example, isophorone, dimethyl adipate, and cyclohexanone. Optionally, a suitable amount of plasticizer, as well as other components, such as fumed silica and silanes can be included in the sodium-selective polymer material. The plasticizer, if included, can be added to the vehicle along with the sodium-selective agent.

Any order of mixing for the polymer material, sodium-selective agent, and plasticizer can be used in preparing the ion-selective membrane of the present invention. Preferably, the sodium-selective agent and plasticizer are added to the vehicle, and fumed silica, if included, is then mulled into the formulation and then the silane, if included, is added. The resulting sodium-selective polymer material can then be used to prepare sodium-selective membranes which, in turn, can be used to prepare sodium-selective electrodes. The production of such electrodes can be achieved using known techniques and methodology. The sodium-selective electrode 5 depicted in FIGS. 1 and 2 is preferred.

The sodium-selective electrode of the present invention can be utilized with other ISE's in multisensor assemblies.

Figure 1:
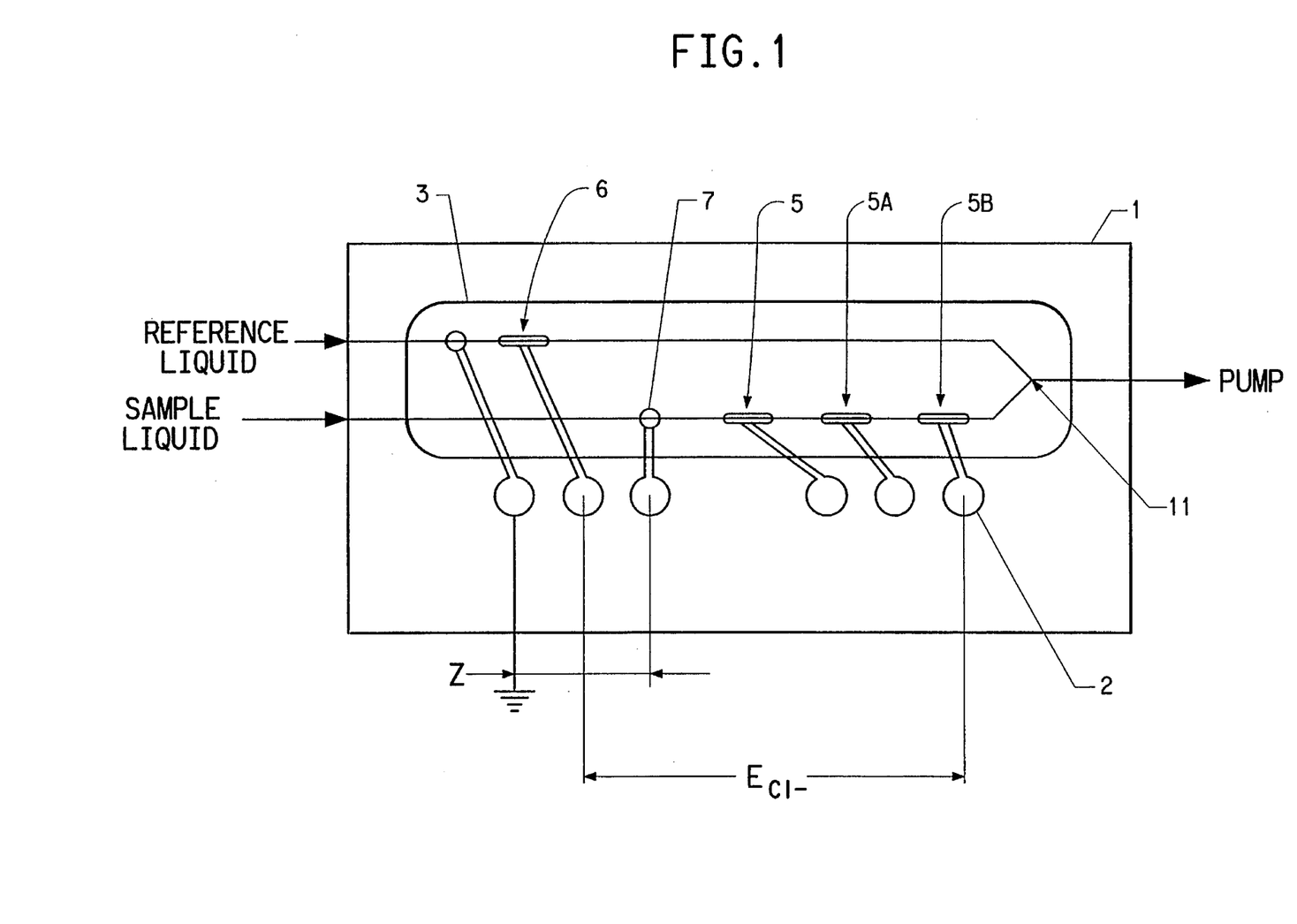
FIG. 1 is a planar view of a multisensor cell assembly having a ceramic substrate with a reference electrode, a chloride ($Cl^-$) selective electrode, a sodium($Na^+$) selective electrode, and a potassium ($K^+$) selective electrode formed thereon.
Figure 2:
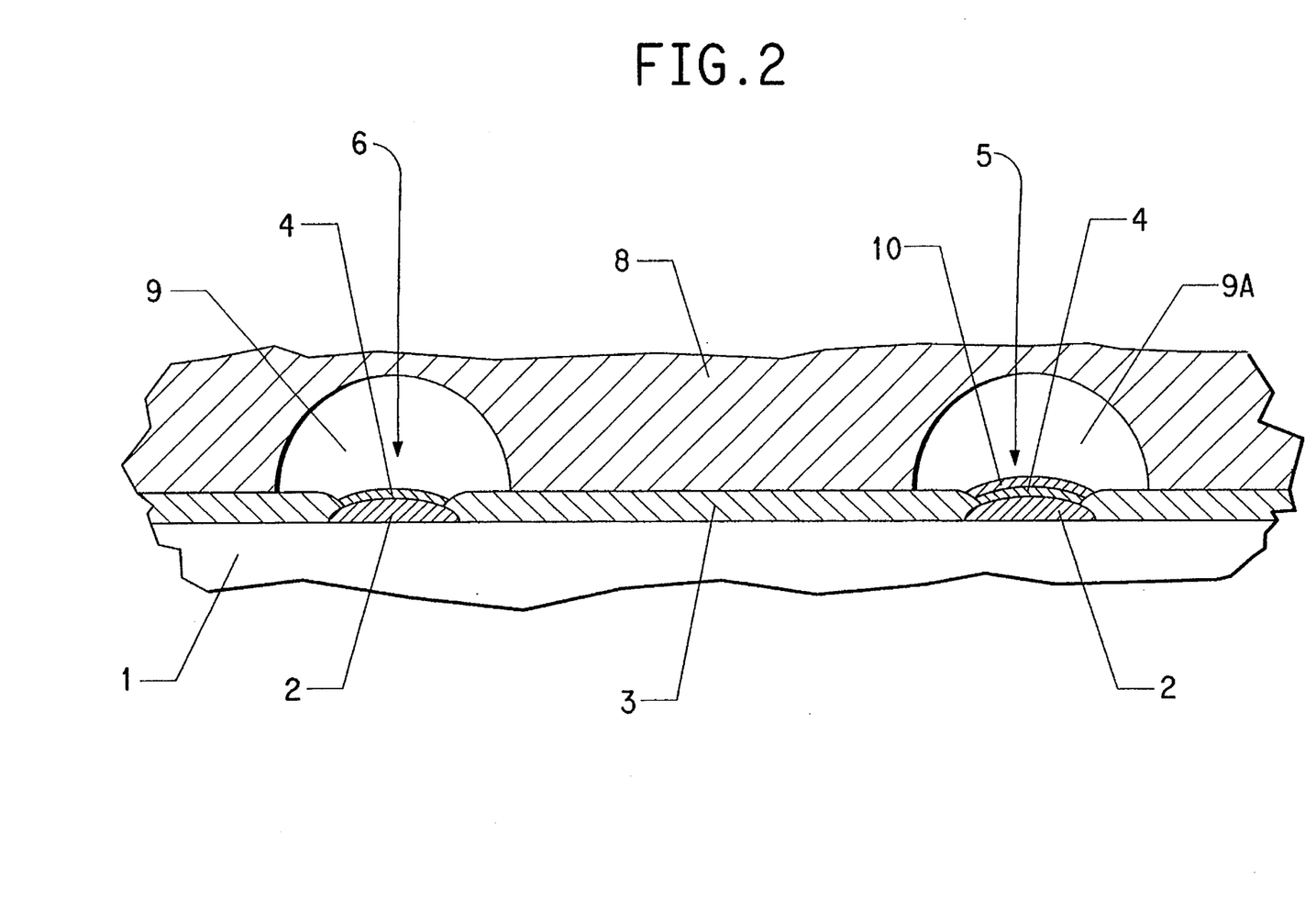
FIG. 2 is a fragmentary cross-sectional view of the multisensor cell assembly of FIG. 1.

For example, FIGS. 1 and 2 depict a multisensor flow cell having a sodium-selective electrode 5 of the present invention. The sodium-selective electrode 5 is formed on a ceramic substrate 1 which is available commercially and can, for example, be purchased from the Coors Ceramics Co. The ceramic substrate 1 has a surface which has been appropriately screen printed with a suitable electrically conductive material (electrical conductor 2) to provide for appropriate electrical contacts for each ion-selective electrode 5, 5A, 5B and a reference electrode 6. Ion-selective electrode 5 is a sodium-selective electrode of the present invention, sensor electrodes 5A and 5B are potassium and chloride ion-selective electrodes, respectively. The electrical conductor 2 can be formed from a silver paste, also available commercially as, for example, silver paste QS175 (E. I. du Pont de Nemours and Company, Del., U.S.). A dielectric layer 3 serves to electrically isolate the electrical conductor 2 and to provide a well for the electrical conductor 2 and an ion-selective membrane 10. A layer composed of a mixture of silver and silver chloride (Ag/AgCl) 4 is screen printed on the electrical conductor 2 for each ion-selective electrode 5, 5A, and 5B and the reference electrode 6. The sodium-selective polymer material prepared, as described above, is positioned onto the silver/silver chloride layer 4 to form the sodium-selective membrane 10. The multisensor assembly can be appropriately fired using known thick film belt techniques after each layer is added.

An elastomeric component 8 is mounted under compression against the electrode bearing substrate 1 to define a reference flow channel 9 and a sensor flow channel 9A and effect a fluid seal along the reference and sample flow channels 9 and 9A. The reference flow channel 9 and sensor flow channel 9A define means for passing reference liquids and sample liquids over the reference 6 and ion-selective electrodes 5, 5A and 5B, respectively. Furthermore, the reference flow channel 9 and sensor flow channel 9A define a common outlet 11, for removing liquids from the cell.

The elastomeric component 8 of the multisensor cell assembly of the present invention can be of any form suitable for defining flow channels 9 and 9A. For example, the multisensor cell assembly of the present invention can be used in conjunction with the disposable sensor assembly or cartridge disclosed in application Ser. No. 07/916,231.

The preferred sodium-selective electrode of the present invention has a membrane comprising about 25% by weight carboxylated polyvinyl chloride, about 9% by weight silane, about 50% by weight dioctyl adipate and about 2% by weight hexadecyl amide monensin or methyl hexyl monensin amide as the sodium-selective agent. Hexadecyl amide monensin is particularly preferred as the sodium-selective agent.

The sodium-selective electrode of the present invention is useful for the potentiometric determination of various ions of interest in biological samples such as blood, urine, plasma, saliva, spinal fluid, and serum. Such samples, particularly urine samples, often contain various interfering substances such as drugs and interfering cations which can interfere with the determination of sodium of interest, i.e., the ion to be determined. Interference with the determination of sodium ion due to the presence of such interfering substances in urine samples can be particularly troublesome.

EXAMPLE 1

A. Synthesis of Hexadecyl Monensin Amide (HMA)

A. Synthesis of Hexadecyl Monensin Amide

An amount of 200.0 mg of sodium monensin ($C_{36}H_{61}O_{11}Na$; 0.2886 mmol; FW=692.9) (Sigma Chemical Co., Mo.) was dissolved in 20 mL chloroform in a 100 mL Erlenmeyer flask.

This solution was extracted twice with 20 mL 1N HCl (20×2 mL) and six times with purified deionized (DI) water (25×6 mL) in a 125 mL separation funnel. The chloroform solution was then dried over magnesium sulfate anhydrous ($MgSO_4$). The dried solution was filtered into a tarred 100 mL round bottle flask and the residue washed with 15 mL chloroform. The combined solution was removed by rotary evaporation. White solid was obtained in about 100% yield (sodium free monensin acid, 193 mg). The solid was dried under vacuum over 3 hours before use.

An amount of 150 mg of the above monensin solid (sodium free monensin acid, 0.2239 mmol) and 63.10 mg disuccinimidyl carbonate (DSC) (FW=256.17; 0.2463 mmol) was placed in a 10 mL vial with magnetic stirrer and capped.

A volume of 5 mL dry tetrahydrofuran (THF) (reagent-grade THF that has been stored over a liberal quantity of 4A molecular sieve for at least 24 hours) was added and the mixture was stirred at room temperature for 15 minutes. Some DSC remained undissolved.

An amount of 32 μL triethylamine (TEA) (FW=101.19; d=0.726) was added and the reaction was stirred for at least 2.5 hrs. The DSC was slowly dissolved during the course of about one hour.

An amount of 54.06 mg (0.2239 mmol) of hexadecyl amine ($CH_3(CH_2)_{15}NH_2$; FW=241.46) (Aldrich Chemical Co., U.S.) was dissolved in 1 mL THF. The resulting hexadecyl amine solution was added to the reaction mixture with stirring. The mixture was then stirred at room temperature for 2 hrs.

B. Purification of Hexadecyl Amide Monensin

The above solution was evaporated to remove the solvent and the residue was redissolved into 1 mL of mixture solvent consisting of 50% ethyl acetate and 50% hexane. The product was purified by column chromatography (a silica gel column of about 2.5×32 cm was used, and the ratio of silica gel to mixture was about 80 to 1 by weight) using a solvent mixture of 50% ethyl acetate and 50% hexane. A thin layer chromatography (TLC) method was developed to monitor the reaction using a mixture of 50% ethyl acetate and 50% hexane as a developing solvent; iodine was utilized to visualize the TLC spots.

The first fraction (TLC, $R_f$=0.4, (50% ethyl acetate and 50% hexane) was collected and the solvents were removed to obtain 95 mg colorless viscous oil of hexadecyl monensin amide (48% total yield from monensin acid).

EXAMPLE 2

Synthesis and Purification of Methyl Hexyl Amide Monensin

The same procedure as described in Example 1 was used to synthesis and purify methyl hexyl amide monensin with the exception that instead of using hexadecyl amine, methyl hexylamine (F.W. 115, Aldrich Chemical Co., U.S.) was used to synthesize the methyl hexyl amide monensin.

EXAMPLE 3

A. Preparation of a Sodium Ion Selective Membrane

An amount of 0.05 g methyl hexyl amide monensin (MHAM) was dissolved in 1.5 grams (g) of the solvent tetrahydrofuran (THF). To this solution was added with stirring 0.97 g dioctyl adipate as a plasticizer. The container was placed in an oven at 80° C. for 15 to 20 minutes to evaporate off the THF.

Into a 400 milliliter (mL) beaker containing 88 grams (g) of the solvent isophorone (Fluka Chemical Co., N.Y., U.S.) was added 12 g of carboxylated polyvinyl chloride (CPVC) (Aldrich Chemical Co., Wisconsin, U.S.). The resulting suspension was covered to prevent evaporation of the solvent and heated using a hot plate/stirrer over a period of about 15 to 20 minutes to a temperature of about 60° C. When the suspension became transparent the heat was turned off and stirring continued for an additional 5 minutes. The resulting polymer material (vehicle) was transferred to a sealed container for subsequent use in preparing a sodium-selective membrane formulation.

An amount of 4.03 g of the vehicle prepared, as described above, was added to the container containing the methyl hexyl amide monensin (MHAM) and dioctyl adipate which was prepared, as described above, (subsequent to the evaporation of the THF) and stirred.

An amount of 0.294 g fumed silica ($SiO_2$) (available from Degussa Co., as Aerosil R972, Ohio, U.S.) was dispersed or mulled into the mixture in the container using a muller (Hoover Automatic Muller Model M5, N.J., U.S.) using three cycles of 20 revolutions each. An amount of 0.17 g silane (3-glycidoxypropyltrimethoxysilane; (Aldrich Chemical Co., catalogue no. 23, 578-4, Wisconsin, U.S.) was then added to the mixture with stirring. The resulting sodium-selective membrane material was subsequently utilized in preparing a sodium-selective electrode.

B. Preparation of Sodium-Selective Electrode

The sodium selective polymer material prepared as described above in A was incorporated into the multisensor flow assembly, illustrated in FIG. 1 as a sodium-selective electrode as follows:

Ceramic substrates (Coors Ceramics Co., Co. U.S.) were ultrasonically cleaned and dried. A silver pattern serving as a conductor was screen printed onto the ceramic substrate using silver paste QS175 (E. I. du Pont de Nemours and Company, Del., U.S.). The ceramic substrates were then fired in a thick film belt furnace such as that commonly used in thick film processing technology, employing a heating rate of 95° C. per minute to 850° C., at 850° C. the ceramic substrates were held for ten (10) minutes and then cooled at a rate of 95° C. per minute. Three layers of thick film dielectric QS482 (E. I. du Pont de Nemours and Company, Del., U.S.) were then screen printed onto the ceramic substrate and dried. The ceramic substrate containing the three dielectric layers was then fired in the thick film belt furnace by employing a heating rate of 95° C. per minute to 850° C., at 850° C. the ceramic substrates were held for ten (10) minutes and then cooled at a rate of 95° C. per minute.

A mixture of silver and silver chloride (90% silver and 10% silver chloride by weight) was then screen printed as layer 4 on the electrical conductor 2 as shown in FIG. 2. The ceramic substrate was then fired by heating at 100° C. per minute to 600° C., holding at 600° C. for ten minutes and cooling at 100° C. per minute. The resulting finished ceramic substrate was then stored in nitrogen until used as follows.

The sodium-selective polymer material prepared as described in Part A above was dispensed using a syringe onto the silver conductor 2 at the sodium-selective electrode location to form the sodium-selective membrane of the sodium-selective electrode depicted in the multisensor flow assembly shown in FIGS. 1 and 2. Similarly, potassium-selective polymer materials and chloride selective polymer materials were dispensed onto the silver conductor 2 at the potassium and chloride-selective electrode locations shown in FIGS. 1 and 2. The sodium-selective material as well as the potassium and chloride-selective polymer materials were then cured by heating the ceramic substrate at 80° C. for 90 minutes to form the sodium-selective membrane. The resulting ceramic substrate assembly was then exposed to an ultraviolet source at an intensity of 750 millijoules per square centimeter. The cured ceramic substrate assembly was then mounted in a cartridge assembly having an elastomer component 8, FIG. 2 and a plastic housing enclosure. The elastomer component 8 is mounted under compression against the electrode bearing substrate to effect a fluid seal along reference and sample flow channels 9 and 9A for reference and sample liquids that flow over the reference 6 and ion selective electrodes 5, 5A, and 5B. An air detect 7 for the multisensor flow assembly provides a means for detecting interfering air bubbles which may be present in the reference and/or sample liquids.

EXAMPLE 4

A. Assay for Sodium Using Sodium-Selective Electrode

The multisensor cell assembly of FIG. 1 was used to compare the sodium-selective membrane electrode formulation of the present invention with known sodium sensor membrane formulations.

The voltage (mV) which changes with varying $Na^+$ concentrations is located at the junction between the sample solution or liquid and the ion-selective membrane. The voltage, E, is defined by the Nernst equation and results from a space charge layer of $Na^+$ ions which develops as a result of the interaction of the ion-selective agent present in the membrane of the sodium-selective electrode.

B. Comparison of Sodium-Selective Electrodes Having Membranes Containing Hexadecyl Amide Monensin With Decyl Ester Monensin Electrodes and Fluka (III) Electrodes Two known sodium-selective membranes were tested in sodium-selective electrodes as follows: Fluka(III) (N,N,N', N'-Tetracyclohexyl-1,2-phenylenedioxydiacetamide, $C_{34}H_{52}N_2O_4$, (available as Fluka Sodium Ionophore (III) (Fluka (III)) from the Fluka Chemical Company, Switzerland), decyl ester monensin, and the hexadecyl monensin amide membrane of the present invention.

The membranes of the Fluka(III), decyl ester monensin and hexadecyl monensin amide electrodes were prepared using the same procedure and same composition as that described in Part A above for the sodium-selective electrode having a membrane containing methyl hexyl amide monensin, with the exception that the ion-selective agent utilized was: Fluka(III) for the Fluka(III) electrode, decyl ester monensin for the decyl ester monensin electrode and hexadecyl monensin amide for the hexadecyl monensin amide electrode.

The selectivity constants for these membranes for sodium relative to potassium were determined to be as follows: Fluka (III): 0.06, Decyl Ester Monensin: 0.2, and Hexadecyl Amide Monensin: 0.12. The selectivity constant is defined by the Nickolskii-Eisenmann equation which defines the contribution of interfering ions to the measured potential. The above selectivities were measured with respect to potassium ions only. While the Fluka(III) membrane electrode provided for the lowest selectivity, the hexadecyl amide monensin electrode provided for better performance with respect to other interfering substances present in urine samples, as shown below.

Figure 3A:
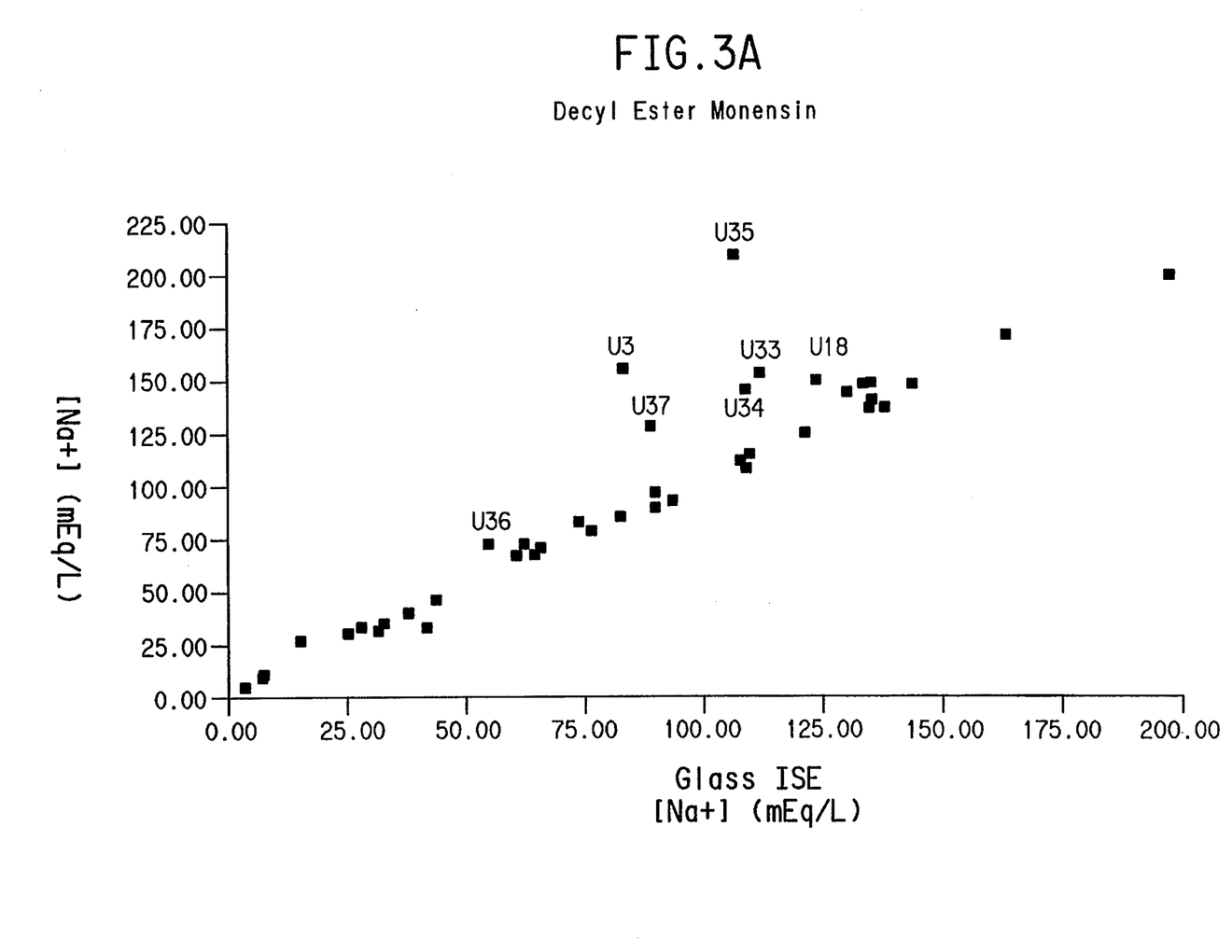
FIG. 3A is a graph depicting a correlation of sodium ion determinations (shown in milliequivalents per liter or mEq/L) made with an ISE having a membrane containing decyl ester monensin with those obtained with a sodium-selective glass membrane electrode.
Figure 3B:
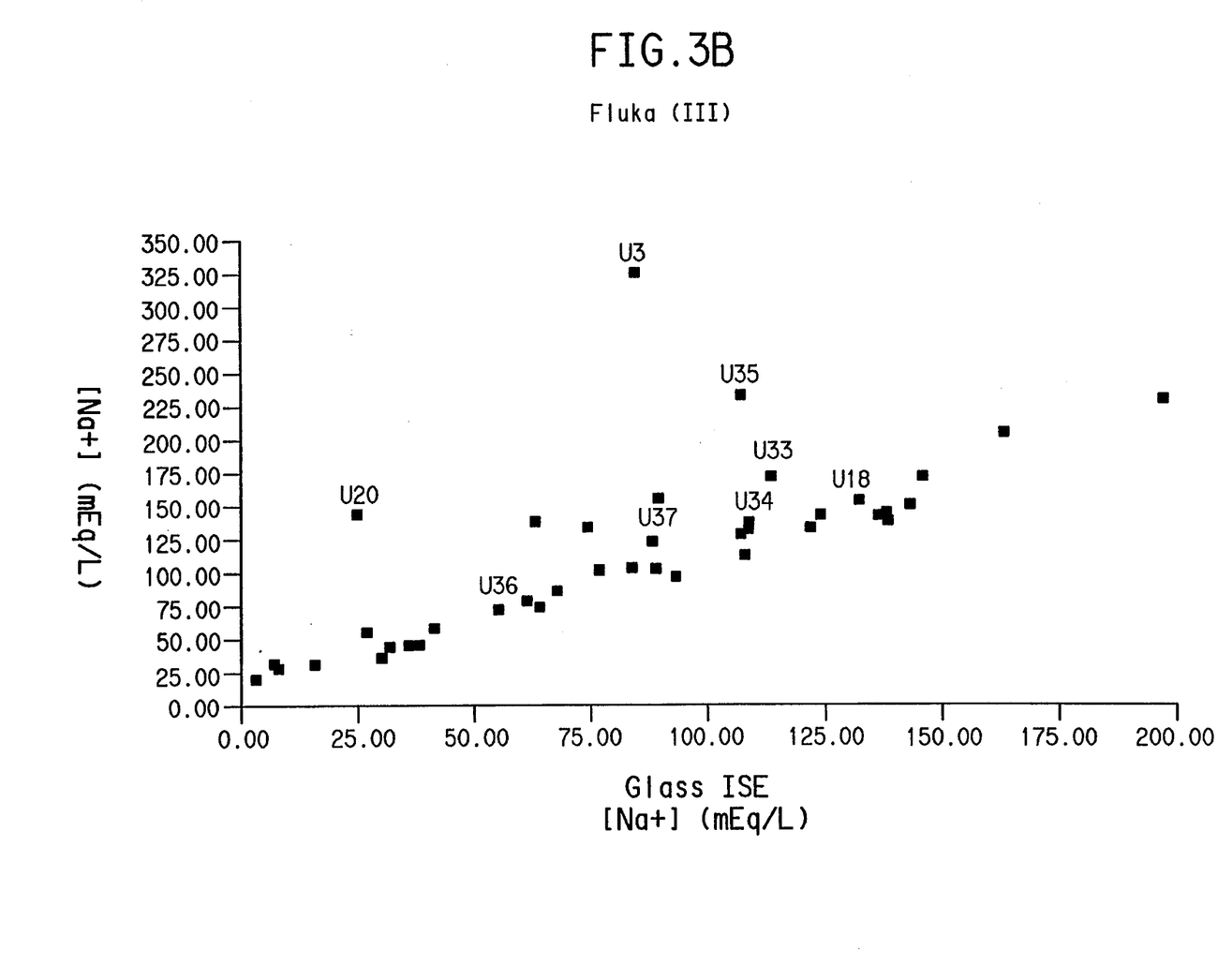
FIG. 3B is a graph depicting a correlation of sodium ion determinations (shown in mEq/L) made with an ISE having a membrane containing Fluka (III) sodium ionophore (N,N,N',N''-Tetracyclohexyl-1,2-phenylenedioxydiacetamide) with those obtained with a glass membrane electrode.
Figure 3C:
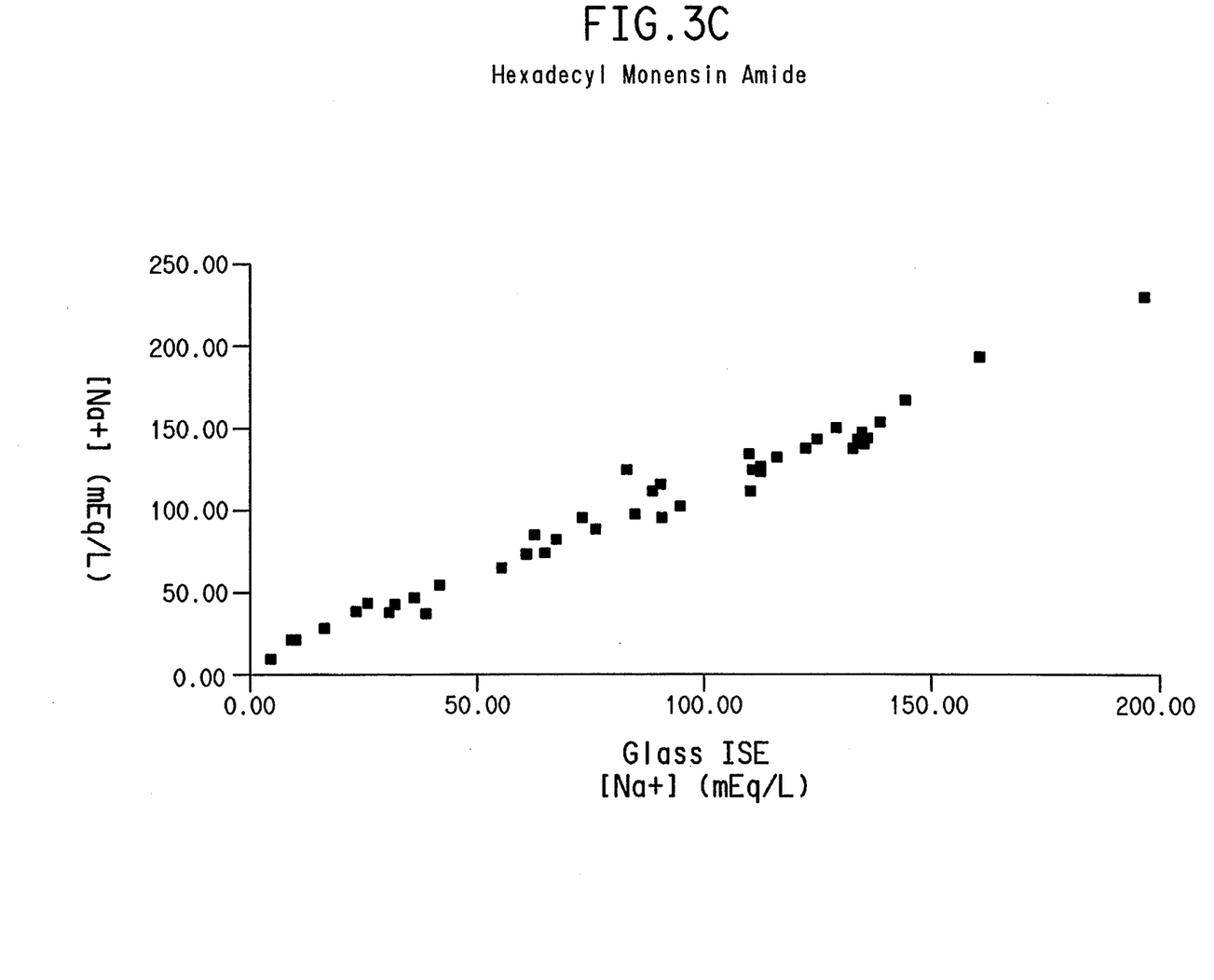
FIG. 3C is a graph depicting a correlation of sodium ion determinations (shown in mEq/L) made with an ISE having a membrane containing hexadecyl amide monensin with those obtained with a glass membrane electrode.

The results are shown in FIGS. 3A, 3B, and 3C. The sodium assays on the membranes prepared with the ionophores were correlated to a sodium-selective glass electrode used on the Dimension® clinical chemistry system analyzer available from E. I. du Pont de Nemours and Company. All correlation assays shown in FIGS. 3A, 3B, and 3C were conducted concurrently using identical samples. The samples employed were human urine samples procured from hospitals, drug clinics, and toxicology laboratories located in Wilmington, Del., and Philadelphia, Pa., U.S. Interfering substances present in urine samples are particularly troublesome in sodium ion determinations. Both the Fluka(III) and decyl ester monensin electrodes show poor performance with some samples, referred to as outlier samples (see for example U3, U37, and U35). FIG. 3C shows the hexadecyl amide monensin electrode outperformed the Fluka (III) electrode (FIG. 3B) and the decyl ester monensin electrode (FIG. 3A) in that all outlier assays, (see for example U3 and U35) were removed with the monensin hexadecyl amide electrode.

Figure 4:
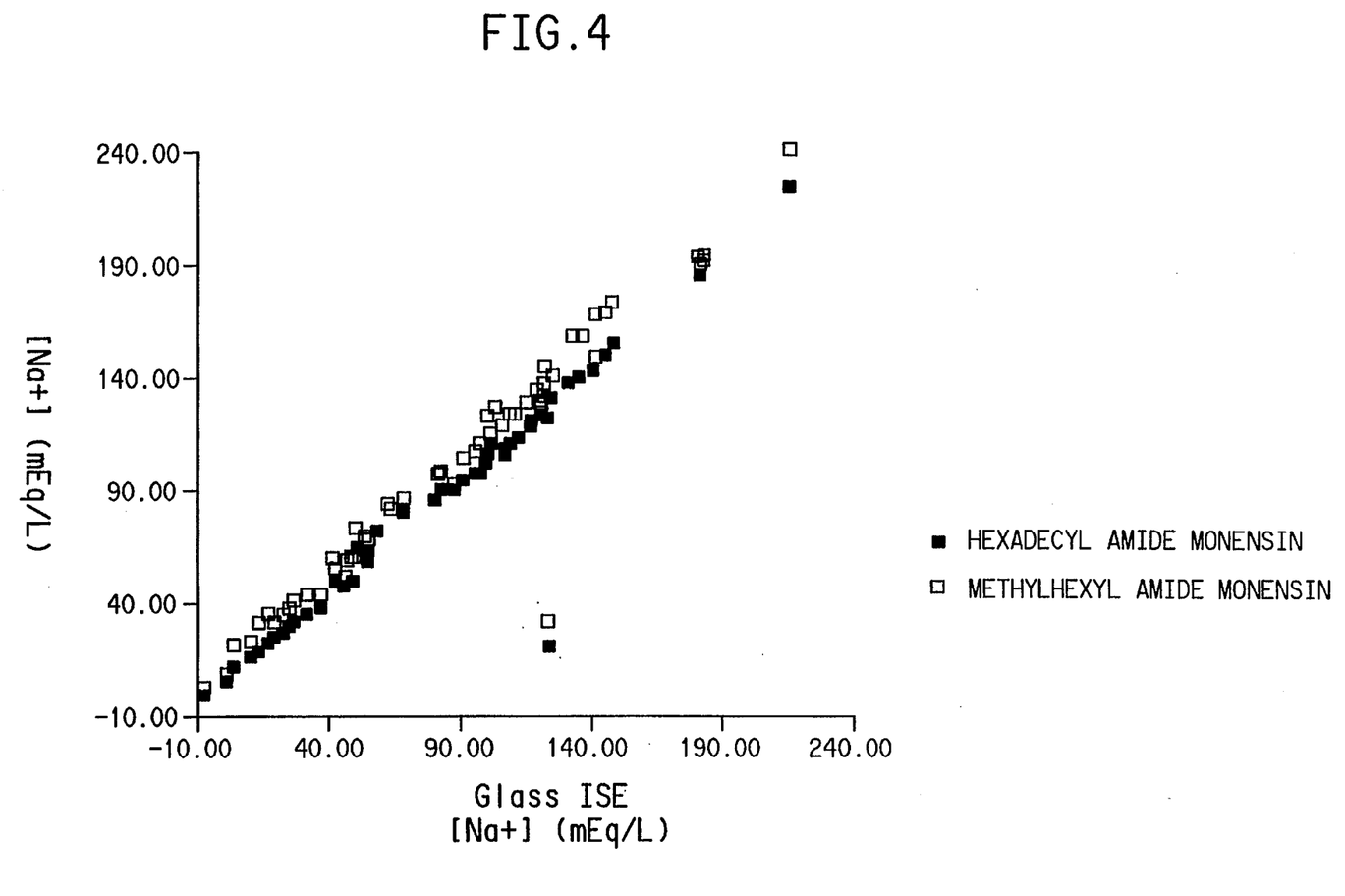
FIG. 4 is a graph depicting a correlation of sodium ion determinations (shown in mEq/L) made with an ISE having a membrane containing methyl hexyl amide monensin and an ISE having a membrane containing hexadecyl amide monensin with those obtained with a glass membrane electrode.

C. Performance of Hexadecyl Monensin Amide and Methyl Hexyl Amide Monensin Electrodes when Correlated with Glass Membrane ISEs Urine samples were tested using the hexadecyl amide monensin and methyl hexyl amide monensin sodium-selective electrodes of the present invention. The results are shown in FIG. 4. The results of FIG. 4 show methyl hexyl amide monensin and hexadecyl amide monensin performed comparably with each other and with a glass membrane electrode.

What is claimed is:

1. A sodium-selective agent useful for determining sodium in biological samples having the structure:

wherein

$R_1$ is H or an alkyl group having less than or equal to six carbon atoms, wherein the alkyl group is straight chained or branched, optionally contains atoms from the group consisting of Oxygen, Sulfur, and Nitrogen; and $R_2$ is an alkyl group having greater than or equal to six carbon atoms wherein the alkyl group is straight chained or branched, optionally contains atoms from the group consisting of Oxygen, Sulfur, and Nitrogen.

2. A sodium-selective agent useful for determining sodium in biological samples having the structure:

3. A sodium-selective agent useful for determining sodium in biological samples having the structure:

4. A sodium-selective electrode for determining an ion in a biological sample which comprises an electrical conductor and an ion-selective membrane separating the conductor from the sample wherein the membrane comprises:
   (a) a polymer material; and
   (b) a sodium-selective agent incorporated into the polymer material, the sodium-selective agent having the structure:

wherein $R_1$ is H or an alkyl group having less than or equal to six carbon atoms, wherein the alkyl group is straight chained or branched, optionally contains atoms from the group consisting of Oxygen, Sulfur, and Nitrogen; and

$R_2$ is an alkyl group having greater than or equal to six carbon atoms wherein the alkyl group is straight chained or branched, optionally contains atoms from the group consisting of Oxygen, Sulfur, and Nitrogen.

5. The sodium-selective electrode of claim 4 wherein the polymer material is selected from the group consisting of polymethyl acrylate and other acrylates, silicone rubbers, polycarbonate cellulose, cellulose ester, poly(vinyl acetate), polyurethane and other urethanes, poly(vinyl butyral), polyvinyl chloride, carboxylated polyvinyl chloride, and other copolymers of vinyl chloride.

6. A sodium-selective electrode for determining sodium in a biological sample which comprises an electrical conductor and an ion-selective membrane separating the conductor from the sample wherein the membrane comprises:
   (a) a polymer material; and
   (b) a sodium-selective agent incorporated into the polymer, the sodium-selective agent having the structure:

7. A sodium-selective electrode for determining sodium in a biological sample which comprises an electrical conductor and an ion-selective membrane separating the conductor from the sample wherein the membrane comprises:
   (a) a polymer material; and
   (b) a sodium-selective agent incorporated into the polymer material, the sodium-selective agent having the structure:

8. The sodium-selective electrode of claims 6 or 7 wherein the polymer material is selected from the group consisting of polymethyl acrylate and other acrylates, silicone rubbers, polycarbonate cellulose, cellulose ester, poly(vinyl acetate), polyurethane and other urethanes, poly(vinyl butyral), polyvinyl chloride, carboxylated polyvinyl chloride, and other copolymers of vinyl chloride.

9. A sodium-selective electrode for determining sodium in a biological sample which comprises an electrical conductor and an ion-selective membrane separating the conductor from the sample wherein the membrane comprises:
   (a) about 25% by weight carboxylated polyvinyl chloride;
   (b) about 2% by weight hexadecyl monensin amide or methyl hexyl amide monensin; and
   (c) about 50% by weight dioctyl adipate.

10. The sodium-selective electrode of claims 1, 6, 7, or 9 wherein the electrical conductor is positioned on an electrically insulative substrate.

11. A multisensor cell assembly for determining an ion of interest in a biological sample comprising:

a substrate having a surface with a reference electrode and at least one ion-selective electrode formed thereon, the ion-selective electrodes having an electrical conductor and an ion-selective membrane separating the conductor from the sample, wherein one ion-selective electrode has a membrane comprising a polymer material and a sodium-selective agent incorporated into the polymer material, the sodium-selective agent having the structure:

wherein $R_1$ is H or an alkyl group having less than or equal to six carbon atoms, wherein the alkyl group is straight chained or branched, optionally contains atoms from the group consisting of Oxygen, Sulfur, and Nitrogen; and $R_2$ is an alkyl group having greater than or equal to six carbon atoms wherein the alkyl group is straight chained or branched, optionally contains atoms from the group consisting of Oxygen, Sulfur, and Nitrogen, an elastomeric component positioned on the surface of the substrate defining a reference and sensor flow channels, the reference flow channel having means for passing reference liquids over the reference electrode, the sensor flow channel having means for passing sample liquids over each ion-selective electrode, the reference and sensor flow channels defining a common outlet for removing liquids from the cell.

12. The multisensor cell assembly of claim 11 wherein the sodium-selective agent is hexadecyl amide monensin.

13. The multisensor cell assembly of claim 11 wherein the sodium-selective agent is methyl hexyl amide monensin.

* * * * *